United States Patent [19]

Gjulling et al.

[11] Patent Number: 4,550,170
[45] Date of Patent: Oct. 29, 1985

[54] 6-PHENYL-2,3,5,6-TETRAHYDROIMIDAZO-[2,1-B]-THIAZOLE DERIVATIVES

[75] Inventors: Eduard V. Gjulling; Larisa A. Djugovskaya; Dmitry I. Zabolotny; Jury P. Kovtun; Nikolai I. Liptuga; Viktor I. Litus; Marina B. Sambur; Nikolai N. Romanov; Alexei I. Tolmachev; Alexandr V. Kirsanov; Viktor N. Pisanko; Oleg F. Melnikov; Evgeny I. Klochkov, all of Kiev, U.S.S.R.

[73] Assignees: Institut Organicheskoi Khimii Akademii Nauk Ukrainskoi SSR; Kievsky Nauchno-Issledovatelsky Institut Otolaringologii, both of Kiev, U.S.S.R.

[21] Appl. No.: 571,465

[22] Filed: Jan. 17, 1984

[51] Int. Cl.$^4$ ............... C07D 513/04; A61K 31/425
[52] U.S. Cl. ............................................. 548/154
[58] Field of Search ......................... 548/154; 424/270

[56] References Cited

U.S. PATENT DOCUMENTS 3,708,490 1/1973 Spicer ..................... 548/154

FOREIGN PATENT DOCUMENTS 910636 11/1980 U.S.S.R. ..................... 548/154

OTHER PUBLICATIONS

Levamizole as Immunomodulator, (Chemistry, Pharmacology, Mechanism of Action and Clinical Applications), Dr. Lajosh Par.

Primary Examiner—Robert Gerstl
Attorney, Agent, or Firm—Ladas & Parry

[57] ABSTRACT

Novel compounds, viz. 6-phenyl-2,3,5,6-tetrahydroimidazo-[2,1-b]-thiazole derivatives have the following general formula:

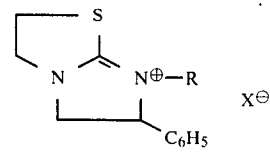

wherein R is $CH_2COOCH_3$, $CH_2COOC_{10}H_{21}$, $CH_2CONH_2$ X is Br.

The compounds possess immunomodulating, antibacterial and antiviral activity.

4 Claims, No Drawings

6-PHENYL-2,3,5,6-TETRAHYDROIMIDAZO-[2,1-B]-THIAZOLE DERIVATIVES

FIELD OF THE INVENTION

The present invention relates to the organic chemistry and, more specifically, to novel chemical compounds - 6-phenyl-2,3,5,6-tetrahydroimidazo-[2,1-b]-thiazole derivatives possessing immunomodulating, antibacterial and antiviral activity and useful as active principles of medicated preparations for the treatment and prophylaxis of infectional and allergic diseases caused by immunal insufficiency.

BACKGROUND OF THE INVENTION

Known in the art are close structural analogs such as 2,3,5,6-tetrahydro-6-phenyl-7-phenacylimidazo-[2,1-b]-thiazolium bromide (cf. USSR Inventor's Certificate No. 910636) and L-(−)-2,3,5,6-tetrahydro-6-phenylimidazo-[2,1-b]-thiazole hydrochloride (levamizole)/Levamizole as Immunomodulator (Chemistry, Pharmacology, Mechanism of Action and Clinical Applications), Dr Alaiosh Par, Chemical Works Gedeon Richter A.G. Budapest, Hungary) mainfesting a stimulating effect in respect of various immunological responses.

This prior art preparation Levamizole, though possessing a broad spectrum of action on the immune system, is toxic and has diverse side effects.

SUMMARY OF THE INVENTION

It is an object of the present invention to provide novel compounds possessing clearly pronounced immunomodulating activity along with antibacterial and antiviral effects which would be useful in medicine as active principles of medicinal preparations.

This object is accomplished by the provision of compounds according to the present invention, viz. 6-phenyl-2,3,5,6-tetrahydroimidazo-[2,1-b]-thiazole derivatives which are novel and hitherto unknown in the literature.

The novel compounds according to the present invention have the following general formula:

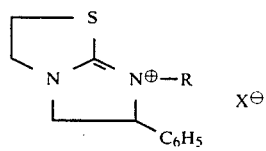

wherein R is $CH_2COOCH_3$, $CH_2COOC_{10}H_{21}$, $CH_2CONH_2$; X is Br.

The compound according to the present invention, i.e. 2,3,5,6-tetrahydro-6-phenyl-7-methoxycarbonylmethylimidazo[2,1-b]-thiazolium bromide has the following formula:

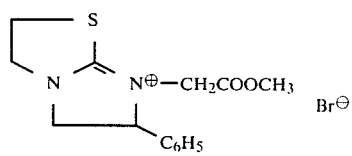

It is a colourless crystalline odourless powder, with the decomposition temperature above 130° C.; it is hygroscopic, soluble in water, lower alcohols, sparingly soluble in acetone, benzene.

The compound according to the present invention viz. 2,3,5,6-tetrahydro-6-phenyl-7-decyloxycarbamoylmethylimidazo-[2,1-b]-thiazolium bromide corresponding to the following general formula:

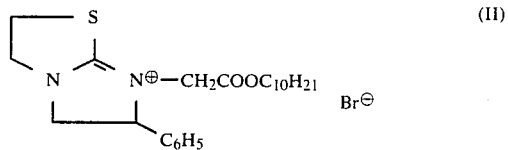

comprises a colourless crystalline odourless powder with the decomposition temperature above 180° C.; it is hydroscopic, soluble in water and lower alcohols.

The compound according to the present invention, viz. 2,3,5,6-tetrahydro-6-phenyl-7-carbamoylmethylimidazo-[2,1-b]-thiazolium bromide corresponding to the following general formula:

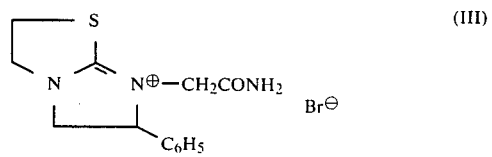

comprises a colourless crystalline powder, with the decomposition temperature above 220° C., well soluble in water, lower alcohols; only slightly soluble in benzene and acetone.

The compounds according to the present invention possess clearly pronounced immunomodulating activity, antibacterial and antiviral effects and can be useful in medicine as active principles of pharmaceutical preparations for the treatment of acute non-specific inflammatory diseases of respiratory tracts and mucous membrane of the mouth cavity in immunodeficient patients, chronical non-specific diseases of respiratory tracts and mucous membrane of the mouth cavity (infectional and allergic rhinitis, tracheitis, bronchitis, tonsillitis, acute herpetic aphthous stomatitis, multi-form exudate erythema, non-specific traumatic ulcera of mucous membranes, ulcero-nectrotic gingivo-stomatitis) focal infections of other localizations.

DETAILED DESCRIPTION OF THE INVENTION

The activity of the compounds according to the present invention was tested experimentally on animals in comparison with the prior art preparation levamizole.

The efficiency of the immunomodulating effect of the novel compounds of this invention was evaluated by comparing their influence on immune responses with that produced by levamizole under similar conditions.

On the basis of the modern conceptions of a special role of antibodies pertaining to the class of immunoglobulins E (IgE) in the pathogenesis of allergic diseases, the effect of the compounds according to the present invention on the production of these antibodies in the respiration organs was studied.

The local production of IgE-antibodies in trachea and lungs of rats of the lines WAY, August with a mass of 250-300 g was induced by means of a successive (with the interval of 40 minutes) dropping a 0.1% solution of histamine and ambrosia allergen (10,000 PNU/ml) into both nasal passages. Aqueous solutions of the compounds according to the present invention (100 and 500 μg/ml) were introduced in a similar manner in portions of 0.05 ml 15 minutes prior to instillation of the allergen. One day after the administration of the allergen IgE-antibodies were determined in homogenates of trachea and lungs prepared at the rate of 0.1 ml of a physiological solution per 10 mg of the tissue by the method of indirect degranulation of obese cells.

It has been found that the compounds of the present invention are capable of inhibiting the formation of the IgE-antibodies in the respiratory organs in concentrations which are by 5 times lower as compared to levamizole (100 μg/ml vs. 500 μg/ml in the case of levamizole).

The test results are shown in the following Table 1.

TABLE 1

Effect of the compounds of the invention on the formation of IgE antibodies in respiratory organs

| Nos. | Groups of animals | Percent of degranulated mastocytes | | Certainty |
|---|---|---|---|---|
| | | Trachea | Lungs | |
| 1 | 2 | 3 | 4 | 5 |
| 1 | Rats given the physiological solution (control) | 20.5 ± 1.1 | 23.6 ± 1.3 | — |
| 2 | Rats given the compound of this invention (I) | | | |
| | 500 μg/ml | 7.0 ± 0.2 | 9.3 ± 0.8 | below 0.05 |
| | 100 μg/ml | 17.8 ± 1.3 | 19.4 ± 1.8 | above 0.05 |
| 3 | Rats given the compound (II) of this invention | | | |
| | 500 μg/ml | 3.5 ± 1.2 | 6.5 ± 0.9 | below 0.05 |
| | 100 μg/ml | 15.0 ± 1.8 | 6.8 ± 0.9 | below 0.05 |
| 4 | Rats given the compound (III) of this invention | | | |
| | 500 μg/ml | 7.1 ± 1.7 | 6.1 ± 1.1 | below 0.05 |
| | 100 μg/ml | 9.1 ± 2.1 | 10.6 ± 3.9 | below 0.05 |
| 5 | Rats given levamizole | | | |
| | 500 μg/ml | 7.4 ± 0.2 | 6.1 ± 1.1 | below 0.05 |
| | 100 μg/ml | 17.3 ± 1.8 | 18.1 ± 1.9 | above 0.05 |

One of the most extensively studied immunomodulating properties of levamizole is its effect on the development of the delayed-type hypersensitivity reactions playing the key role in pathogenesis of allergic, inflammatory and oncological diseases. Such reactions were caused by application, onto a shaven surface of the abdomen of CBA mice, of 0.1 ml of a 0.5% solution of dinitrochlorobenzene in acetone. 14 days thereafter, onto the left (test) ear of the mice one drop of the same solution was applied, while on the right (control) ear—one drop of acetone. The response was assessed 24 hours there after the difference in thickness of the left and right ears of the test animals. The compounds according to the present invention and levamisol were administered to the mice per os for five times, once per 3 says, starting with the day of sensitization, in the doses of 2.5 mg/kg and 25 mg/kg. The control group was administered an equal volume of a physiological solution. The data were statistically processed using the non-parametric "U" criterion by Wilkoxon-Mann-Whitney; the thus-obtained results are shown in Table 2 hereinbelow.

It has been shown that levamizole inhibits the development of the contact hypersensitivity only when administered in the dose of 25 mg/kg, whereas compounds (II) and (III) according to the present invention actively inhibit the studied reaction both in the dose of 25 mg/kg and in the dose of 2.5 mg/kg, i.e. for inhibition of the contact hypersensitivity it is sufficient to administer preparations in a dose which is by 10 times lower than that of levamizole.

TABLE 2

Effect of levamizole and the compounds of this invention on the development of an allergic reaction of the delayed type in mice.

| | | Ear thickness, μm | | | | | |
|---|---|---|---|---|---|---|---|
| | | Experiment | | Control | | | |
| Nos. | Preparation | Average value | Range of fluctuations | Average value | Range of fluctuations | Number of tests | Certainty |
| 1 | 2 | 3 | 4 | 5 | 6 | 7 | 8 |
| 1 | Physiological solution | 203.0 | 130–260 | 168.0 | 120–190 | 10 | <0.05 |
| 2 | Levamizole | | | | | | |
| | 2.5 mg/kg | 210.0 | 160–280 | 162.3 | 130–200 | 7 | <0.05 |
| | 2.5 mg/kg | 179.2 | 170–190 | 179.2 | 160–190 | 6 | >0.05 |
| 3 | Compound (II) of this invention | | | | | | |
| | 2.5 mg/kg | 222.8 | 175–300 | 202.2 | 150–250 | 9 | >0.05 |
| | 25 mg/kg | 184.4 | 170–240 | 178.9 | 150–240 | 9 | >0.05 |
| 4 | Compound (III) of this invention | | | | | | |
| | 2.5 mg/kg | 184.4 | 110–220 | 176.7 | 110–210 | 9 | >0.05 |
| | 25 mg/kg | 190.0 | 170–200 | 184.4 | 170–200 | 9 | >0.05 |

The effect of the compound (I) of the present invention on the development of the delayed-type hypersensitivity reaction was studied by means of the procedure proposed by E. V. Gulling and M. B. Sambur (1981).

Mice were sensitized by introducing into pads of both hind limbs $10^4$ rat's thymocytes killed by heating (at 56° C. for 20 minutes). The reaction was assessed by the difference in the mass of popliteal lymph nodes in the control and test limb 24 hours after the absolving injection ($10^6$ rat's thymocytes, heated) which was effected on the 5-th day of the experiment.

In guinea pigs such reaction was simulated by means of double (with the interval of 14 days) administration, into the pads of hind limbs, of 0.1 mg of a 0.4% solution of 2,4-dinitrochlorobenzene in a 25% ethanol. The reaction was assessed by the difference in temperature of the pad surfaces and thickness of talipes of hing limbs 24 hours after the absolving injection of the antigen.

The effect of the compound according to the present invention as compared to levamizole was studied in concentrations of 100, 500 and 1,000 μg/ml upon introduction thereof into the left hind limb's pad in the volume of 0.05 ml 4 hours prior to the sensitization (mice) and in the volume of 0.2 ml 24 hours prior to the sensitizing and absolving injections (guinea pigs).

At the same time, into the left hind limb's pad a physiological solution is introduced in the volume of 0.05 ml (mice) and 0.1 ml (guinea pigs).

The thus-obtained results are shown in Table 3 hereinbelow.

In the in vitro experiments the effect of the compound (III) according to the present invention and levamizole on activation of human tonsillocytes was studied.

The cytolytic effect of tonsillocytes was studied by the radioisotope method using $Cr^{51}$. On doing so, the deterioration of target cells (chicken's erythrocytes) by tonsil lymphocytes was regarded as spontaneous cytolysis, while the destruction of the target cells loaded, in addition to the isotopic tracer, with homologous antibodies in the sublytic dose was considered as antibody-dependent cytolysis. The preparations were used in the final concentration of 1 μg/ml, 10 and 100 μg/ml; $10^7$ cells of tonsils were cultured for 1 hour at the temperature of 37° C. with the preparations under sterile conditions. Afterwards they were twice washed by means of

TABLE 3

| Nos. 1 | Concentration of the preparation 2 | Difference in temperature of the pad surfaces and thickness of control and test talipes of the hind limbs in guinea pigs | | Number of animals 5 | Difference in masses of popliteal lymph nodes in the control and test limb in mice, mg Average value 6 | Number of animals 7 |
|---|---|---|---|---|---|---|
| | | Temperature, °C. Average value 3 | Thickness, mm Average value 4 | | | |
| 1 | Levamizole 100 μg/ml | −1.3 ± 0.06* | −0.75 ± 0.08* | 7 | −0.9 ± 0.13* | 8 |
| 2 | Compound (I) of this invention 100 μg/ml | −1.5 ± 0.27* | −0.6 ± 0.062* | 7 | −1.1 ± 0.08* | 7 |
| 3 | Levamizole 500 μg/ml | | | | +1.0 ± 0.13 | 11 |
| 4 | Compound (I) of this invention 500 μg/ml | | | | +1.3 ± 0.2 | 7 |
| 5 | Levamizole | +1.1 ± 0.11 | +0.51 ± 0.064 | 9 | +1.2 ± 0.12 | 11 |
| | Compound (II) of this invention, 1,000 μg/ml | +1.2 ± 0.16 | +0.63 ± 0.09 | 7 | +1.3 ± 0.29 | 7 |

*The difference was regarded as negative in the case where the test values exceeded the control ones.

From the results shown in the above Table 3 it follows that in the concentration of 100 μg/ml the compound (I) of the present invention, likewise levamizole, surely stimulates and in concentrations of 500 and 1,000 μg/ml effectively inhinits the development of the delayed-type hypersensitivity reactions.

It should be noted that the immunomodulating properties of the test compound according to the present invention are slightly more pronounced than those of levamizole.

An important characteristic of the immunomodulating effect of levamizole is its influence on the cytolytic activity of T-cells. On this basis, the effect of one of the lest toxic compound (III) out of those of the present invention was studied for the antibody-dependent cytolytic activity of cells.

Medium 199 using centrifugation (105 g, 10 minutes). Then the tonsillocytes were added with corresponding target cells and cultured for 18-20 hours at 37° C. The degree of destruction of the target cells was determined radiometrically by the outcome of $Cr^{51}$ into the liquid phase.

It has been shown that the compound (III) of the present invention stimulates the antibody-dependent cytolytic activity in concentrations which are 10-100 times lower as compared to those of levamizole (1-10 μg/ml compared to 100 μg/ml for levamizole).

The activity of natural killers of tonsil cells was promoted only by the compound (III) of the present invention when used in the concentration of 1 and 10 μg/ml The activity of natural killers under the effect of levamizole have not noticeably changed. The test results are shown in Table 4 hereinbelow.

TABLE 4

| | | Effect of immunomodulators on natural and antibody-dependent cytotoxicity of human tonsillocytes | | | | | |
|---|---|---|---|---|---|---|---|
| Nos 1 | | Statistical characteristics Experiment 2 | Yield of $^{51}$Cr from target cells (6%) | | | | |
| | | | Levamizole | | | Compound (III) of this invention | | |
| | | | 1 μg/ml 3 | 10 μg/ml 4 | 100 μg/ml 5 | 1 μg/ml 6 | 10 μg/ml 7 | 100 μg/ml 8 |
| 1 | Natural cytotoxicity | Average value | 16.2 | 18.4 | 20.5 | 30.6* | 28.8* | 24.8* |
| 2 | | Range of fluctuations | 3.0–41.0 | 5.0–53.0 | 5.0–49.0 | 7.0–60.0 | 7.0–42.0 | 1.0–40.0 |
| 3 | | n-number of tests | 8 | 8 | 8 | 8 | 8 | 8 |

TABLE 4-continued

Effect of immunomodulators on natural and antibody-dependent cytotoxicity of human tonsillocytes

| Nos 1 | Statistical characte- ristics Experiment 2 | Yield of $^{51}$Cr from target cells (6%) | | | | | |
|---|---|---|---|---|---|---|---|
| | | Levamizole | | | Compound (III) of this invention | | |
| | | 1 μg/ml 3 | 10 μg/ml 4 | 100 μg/ml 5 | 1 μg/ml 6 | 10 μg/ml 7 | 100 μg/ml 8 |
| 4 | control | | 13.3 5.0–28.0 | | | | |
| 5 | Antibody dependent cytotoxi- city average | 14.0 | 14.2 | 22.8* | 23.2* | 22.6* | 19.1 |
| 6 | Range of fluc- tuations | 1.0–32.0 | 1.0–36.0 | 8.0–39.0 | 10.0–57.0 | 13.0–36.0 | 4.0–40.0 |
| 7 | n - number of tests | 8 | 8 | 8 | 8 | 8 | 8 |
| 8 | Control | | 10.7 3.0–34.0 | | | | |

*Statistically certain relative to the control (P below 0.05).

Since the effect of immunomodulators on proliferation and differentiation of lympocytes is realized through a system of cyclic nucleophyls, as one of the principal indicators of the efficiency and mechanism of their action their effect on the level of cyclic adenosinemonophosphate (c-AMP) and cyclic guanosinemonophosphate (c-GMP) can be regarded. As it has been experimentally shown, under the effect of levamizole, likewise compound (III) of the present invention, reciprocal variations of concentrations of c-AMP and c-GMP are observed which is likely to reflect a characteristic periodicity of activation of cyclases during the cell cycle. The reduced content of c-AMP in splenocytes caused by immunomodulators is combined with a considerable increase, in these cells, of the activity of phosphodiesterase of c-AMP, the level of which is in a direct relationship with the compound concentration.

One of the indications of the expediency of a therapeutic administration of immunomodulators is an increase in sensitivity of lympocytes of patients to a particular preparation; for the determination thereof the method of E-rosella formation was used.

The results of the effect of levamizole and the compounds of the present invention on lymphocytes was evaluated from the extent of the efficiency of a preliminary incubation of lymphocytes in patients with infectional-allergic rhinitis using different concentrations of the preparation in elevation of their capacity of forming rosellae with ram's erythrocytes.

The test results have shown that the compounds according to the present invention are in no case less effective and they are capable, in the same concentrations as levamizole, of certainly increasing the number of E-rosella forming cells. The compounds of the present invention are also capable of inducing the formation of interferon.

For the study of interferon-formation in vivo, the compound (III) of the present invention was intranasally administered in doses of 1 and 10 μg per mouse in the volume of 0.1 ml. The experiments were carried out on mice of the line C57W. After 6, 24, 72 and 168 hours the mice's blood serum was investigated for the presence of interferon. Indication of interferon was effected on grafted mouse cells L against 100 TCD$_{50}$ virus of vesicular stomatitis. For the purpose of control, mouse interferon induced in the animals by the intraperitoneal injection of the Newcastle disease virus was titrated in parallel.

The test results are shown in Table 5 hereinbelow.

TABLE 5

Titres of interferon in mice serum within different time limits after the administration of levamizole and the compound (III) of the present invention

| Administered preparations | | Time after administration of preparations, hrs | | | |
|---|---|---|---|---|---|
| | | 6 | 24 | 72 | 168 |
| Levamizole | 1 μg | 160 | 40 | 40 | 80 |
| | 10 μg | 160 | 40 | 40 | 80 |
| Compound (III) of the present invention | 1 μg | 320 | 80 | 160 | 160 |
| | 10 μg | 320 | 80 | 80 | 160 |

The results demonstrate that the compound (III) according to the present invention is a more active inductor of interferon in vivo as compared to levamizole.

Also studied was the effect of the compounds (II) and (III) of the present invention, as well as levamizole on reproduction of the virus of vesicular stomatitis and grafted culture of kidneys of green marmoset - vero.

The preparations were introduced into a nutrient medium of the cultured cells in non-toxic doses of 10.1 and 0.1 μg/ml. The cells were kept for 24 hours at the temperature of 37° C., whereafter the virus with the infection multiplicity 10 TCD$_{50}$ was introduced. The control cells under similar conditions were treated with a sterile medium.

24–28 hours after a complete degeneration of the cell stratum under the action of the virus the control and test cells were twice frozen and centrifuged at 1,500 r.p.m. for 20 minutes and the titre of the reproduced virus was determined in the liquid over the residue. The test results are shown in the following Table 6.

TABLE 6

Effect of the compounds according to the present invention on reproduction of the virus of vesicular stomatitis

| Preparation | | Degree of inhibition of the virus reproduction |
|---|---|---|
| Levamizole | 1 μg/ml | 0 |
| | 10 μg/ml | 10 times |
| Compound (III) of this invention | 1 μg/ml | 10 times |
| | 10 μg/ml | 100 times |
| Compound (II) of this | 1 μ/ml | 10 times |

TABLE 6-continued

Effect of the compounds according to the present invention on reproduction of the virus of vesicular stomatitis

| Preparation | Degree of inhibition of the virus reproduction |
|---|---|
| invention | 10 μg/ml | 100 times |

As it is seen from the data shown in the above Table, the compounds according to the present invention (II) and (III) are ten times more active than levamizole in respect of inhibition of reproduction of the virue of vesicular stomatitis in the culture.

In the experiments in vitro the antibacterial activity of the compounds of the present invention was studied. To this end, serial dilutions of compounds (II) and (III) with a concentration of from 1% to 0.00001% were prepared and 0.1 ml of a microbal suspension was added thereto (*Staphylococcus aureus*, Proteum, *Bacillus pyocyanes*). The microbal load for staphylococcus was about $1 \times 10^5$ cells/ml, for Proteum and *Bacillus pyocyanes* $-1 \times 10^4$c cells/ml.

As the control, antibiotics with a broad range of action and levamizole were used. The bacteria were incubated along with the compounds according to the present invention at the temperature of 37° C. After 1.3 and 24 hours samples were taken by 0.1 ml from a corresponding dilution of the compounds for the determination of the number of viable bacteria in the culture. Inoculations were effected by spreading 0.1 ml of a suspension of bacteria in a corresponding dilution of the compounds over the surface of an agar dish using a glass spatula.

It has been shown that the highest antibacterial activity is inherent in the compound (II) of the present invention the inhibiting concentration is 1-12.5 μg/ml, whereas the activity of levamizole and compound (III) is lower by a factor of 2.

The basic obstacle hindering a broad practical application of levamizole in the clinical practice is its high toxicity and a high frequency of the observed side effects. For this reason a detailed comparative study of toxicity of the novel compounds was carried out.

The $LD_{50}$ was determined on mice of the CBA line of both sexes with a mass of 20–21 g. The compounds were administered to the mice subcutaneously in the volume of 0.5 ml. The results were evaluated following the procedure by Kerber and Pershin. It has been found that the $LD_{50}$ for compound (I) upon its subcutaneous administration is 262.2 mg/kg, for compound (II)—166.7 mg/kg, for compound (III)—1,016.7 mg/kg as compared to 121 mg/kg for levamizole.

Therefore, the compounds according to the present invention are considerably less toxic as compared to levamizole. Especially promising in this respect is compound (III). The studies of its "acute" toxicity on rats (Wistar line, mass 180–200 g), guinea pigs (mongrel, mass 200–300 g) and rabbits (mass 2–2.5 kg) have proven its advantages as demonstrated by the data of the following Table 7.

TABLE 7

| Animal species and sex | $LD_{50}$ upon subcutaneous injection, mg/kg | | $LD_{50}$ upon peroral administration, mg/kg | |
|---|---|---|---|---|
| | Levamizole | Compound (III) of the invention | Levamizole | Compound (III) of the invention |
| Rats | | | | |
| ♂ | 136.7 | 2,584.0 | 533.4 | 5,749.4 |
| ♀ | 116.7 | 1,416.7 | 400.0 | 3,500.0 |
| Rabbits | 38.4 | 316.7 | 266.7 | 3,333.4 |

The effect of compound (III) according to the present invention on the general condition of the animals, composition of their peripheral blood was studied along with the functional state of the central nervous system, cardio-vascular and respiratory systems, liver, kidneys, as well as the mass and morphological structure of the inner organs.

Prior to the beginning of the experiments over one week the initial characteristics of the peripheral blood, function of the central nervous system, cardio-vascular system, respiration, liver and kidneys were determined for three times.

The animals were slaughtered 30 days thereafter and subjected to pathomorphological investigation (with histological analysis of the organs).

The tests were performed on 20 mature rats with a mass of 180 to 200 g. The animals were daily given 1/10 of the $LD_{50}$ of the preparation.

According to the data of the studies thus performed, one month administration of the preparation to rats causes no toxic phenomena in them. During this period the animals had a normal bodyweight gain.

No statistically certain differences were revealed in the functional state of the vitally important systems of the organism (central nervous system, cardi-vascular and respiratory systems) in the animals after a month administration of the compound according to the present invention, thus demonstrating its harmlessness. This is also evidenced by the absence of an essential influence of the compound on the quantitative and qualitative composition of cells of the peripheral blood (insignificant fluctuations were not beyond the known limits of the physiological norm and did not differ from those in the control animals), on the function of liver determined through the ability of liver cells to entrain a dye - bromosulphophthalein.

The performed experimental studies demonstrate that the compounds according to the present invention pertain to the group of substantially harmless substances possessing toxicity considerably smaller than that of levamizole. At the same time they provide a clearly pronounced dose-dependent effect on the state of the immune system which is not inferior (and as regards some characteristics such as hypersensitivity reactions of the delayed and non-delayed types, spontaneous and anti-body-dependent cytotoxicity) even superior to the effect of a known immunotropic preparation - levamizole producing their effect in concentrations by 5–10 times and even more times smaller than those of levamizole. Furthermore, the compounds according to the present invention have a more pronounced, as compared to levamizole, antiviral and antibacterial activity and comprise active inductors of interferon in vivo.

The compounds according to the present invention, viz. 6-phenyl-2,3,5,6-tetrahydroimidazo-[2,1-b]-thiazole derivatives are produced by a process based on a known reaction of tertiary amines with haloalkyls; they comprise colourless hydroscopic powders.

For a better understanding of the present invention, some specific examples illustrating preparation of the compounds according to the present invention are given hereinbelow.

EXAMPLE 1

2 g (0.01 mol) of 2,3,5,6-tetrahydro-6-phenylimidazo-[2,1-b]-thiazole are dissolved in 20 ml of acetone and added with 1.53 g (0.01 mol) of methyl ester of monobromacetic acid. After 12 hours the residue is filtered-off and washed with acetone to give 2.86 g (81%) of 2,3,5,6-tetrahydro-6-phenyl-7-methoxycarbonylmethylimidazo-[2,1-b]-thiazolium bromide melting at 81°–82° C. (from dioxane).

Found, %: Br 22.0; S 8.8. Calculated, %: Br 22.4; S 9.0. $C_{14}H_{17}BrN_2O_2S$.

UV spectrum: in methanol the maximum of absorption is above 220 nm (in the absorption band of the solvent).

IR spectrum (KBr): 1,720 cm$^{-1}$ (CO).

PMR in $CF_3COOH$, HMDS (hexamethyldisilozane)—external standard (δ), ppm: 3.67, s, 3H; 3.80–4.63, m, 6H; 5.60, t, 1H; 7.30 s, 5H.

EXAMPLE 2

2 g (0.01 mol) of 2,3,5,6-tetrahydro-6-phenylimidazo-[2,1-b]-thiazole and 2.8 g (0.01 mol) of decyl ester of monobromacetic acid are dissolved in 25 ml of acetone and allowed to stand overnight at room temperature. The product is filtered-off and washed with acetone to give 4.6 g (96%). After crystallization from dioxane there are obtained 3.6 g (75%) of 2,3,5,6-tetrahydro-6-phenyl-7-decyloxycarbonylmethylimidazo-[2,1-b]-thiazolium bromide, m.p. 127°–128° C.

Found, %: Br 17.2, H 6.8, N 5.9. $C_{23}H_{34}BrN_2O_2S$. Calculated, %: Br 16.5, H 6.6, N 5.2.

UV spectrum: in methanol the maximum of absorption is above 220 nm (in the absorption band of the solvent).

IR spectrum (KBr): 1,720 cm$^{-1}$ (CO).

PMR in $CF_3COOH$, HMDS - external standard (δ), ppm: 0.93–1.63 m, 19H; 3.70–4.67 m, 8H; 5.70-t, 1H; 7.46, s, 5H.

EXAMPLE 3

To a solution of 2 g (0.01 mol) of 2,3,5,6-tetrahydro-6-phenyl-imidazo-[2,1-b]-thiazole in 10 ml of acetone a solution of 1.4 g (0.01 mol) of bromacetamide in 10 ml of acetone is added upon cooling and stirring. The resulting precipitate is filtered-off and crystallized from an alcohol to give 2.4 g (70%) of the product with m.p. 214°–215° C.

Found, %: Br 23.54, S 9.42, $C_{13}H_{16}BrN_3O_3S$. Calculated, %: Br 23.35, S 9.37.

UV spectrum: in methanol the maximum of absorption is above 220 nm (in the absorption band of the solvent).

IR spectrum (KBr): 1,695 cm$^{-1}$ (CO), 3,100–3,300 cm$^{-1}$ (N-H).

PMR in $CF_3COOH$, HMDS—external standard (δ), ppm: 3.63–4.56, m, 8H; 5.56, t, 1H; 7.30, s, 5H.

What is claimed is:

1. 6-Phenyl-2,3,5,6-tetrahydroimidazo-[2,1-b]-thiazole derivatives of the general formula:

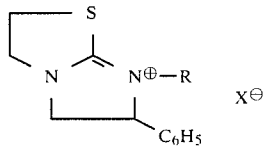

wherein R is $CH_2COOCH_3$, $CH_2COOC_{10}H_{21}$, $CH_2CONH_2$; X=Br.

2. 2,3,5,6-Tetrahydro-6-phenyl-7-methoxycarbonylmethylimidazo-[2,1-b]-thiazolium bromide according to claim 1, having the formula:

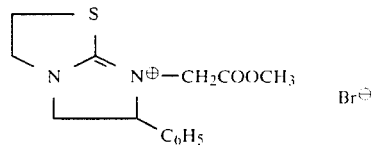

3. 2,3,5,6-Tetrahydro-6-phenyl-7-decyloxycarbonylmethylimidazo-[2,1-b]-thiazolium bromide according to claim 1, having the formula:

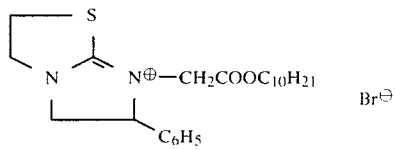

4. 2,3,5,6-Tetrahydro-6-phenyl-7-carbamoylmethylimidazo[2,1-b]-thiazolium bromide according to claim 1, having the formula:

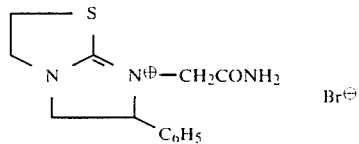

* * * * *